(12) United States Patent
Shaddock et al.

(10) Patent No.: US 7,739,898 B2
(45) Date of Patent: Jun. 22, 2010

(54) SYSTEM AND METHOD FOR OPERATING AN EXHAUST GAS SENSOR SYSTEM

(75) Inventors: David Mulford Shaddock, Troy, NY (US); Ganapathisubbu Sethuvenkatraman, Sholavandan (IN); Kunal Ravindra Goray, Bangalore (IN)

(73) Assignee: General Electric Company, Niskayuna, NY (US)

( * ) Notice: Subject to any disclaimer, the term of this patent is extended or adjusted under 35 U.S.C. 154(b) by 951 days.

(21) Appl. No.: 11/166,422

(22) Filed: Jun. 24, 2005

(65) Prior Publication Data
US 2006/0289308 A1      Dec. 28, 2006

(51) Int. Cl.
*G01N 27/26* (2006.01)

(52) U.S. Cl. ...................... 73/31.05; 73/23.31

(58) Field of Classification Search .............. 73/23.2, 73/23.31, 31.05; 204/424, 426, 428, 431
See application file for complete search history.

(56) References Cited

U.S. PATENT DOCUMENTS

| | | | |
|---|---|---|---|
| 4,656,832 A | | 4/1987 | Yukihisa et al. |
| 4,818,363 A | | 4/1989 | Bayha et al. |
| 4,929,331 A | * | 5/1990 | Kato et al. ............... 204/426 |
| 6,015,533 A | * | 1/2000 | Young et al. ............... 422/83 |
| 6,572,682 B2 | | 6/2003 | Peter et al. |
| 6,637,254 B2 | | 10/2003 | Wagner et al. ............ 73/31.05 |
| 6,691,553 B2 | | 2/2004 | Holleboom |
| 6,712,884 B2 | | 3/2004 | Brück et al. |
| 6,749,732 B2 | * | 6/2004 | Nakagawa et al. ......... 204/428 |
| 6,780,298 B2 | * | 8/2004 | Nakamura et al. ......... 204/428 |

* cited by examiner

*Primary Examiner*—Daniel S Larkin
(74) *Attorney, Agent, or Firm*—Patrick K. Patnode (57) ABSTRACT

An exhaust gas sensor system includes an inner chamber disposed around a sensor element. The inner chamber has either a cylindrical shape or a frusto-conical shape. The system further includes an outer chamber disposed substantially around the inner chamber to redirect a flow of an exhaust gas stream having an original direction by allowing the exhaust gas stream to strike a surface of the inner chamber to change the original direction of the flow to a substantially perpendicular direction relative to the original direction, then to substantially reverse the substantially perpendicular direction of the flow to create a substantially reversed flow within the inner chamber. Alternately the exhaust sensor system includes a sintered metal filter that prevents exhaust gas particles from fouling a sensor element. The system further includes an electric source coupled to the sintered metal filter to heat the sintered metal filter to a temperature sufficient to remove the exhaust gas particles from the sintered metal filter.

13 Claims, 7 Drawing Sheets

SYSTEM AND METHOD FOR OPERATING AN EXHAUST GAS SENSOR SYSTEM

BACKGROUND

The invention relates generally to an exhaust gas sensor system and, more specifically, to a system and method for protecting an exhaust gas sensor from particulate emissions.

Vehicle and industrial exhaust emissions typically include carbon monoxide, oxides of nitrogen, hydrocarbons and particulates, carbon dioxide, or the like. These substances are a significant contributor to local air pollution, which may result in poor visibility, including smog, and haze and erosion of building surfaces.

Because of concerns about pollution, many vehicles and industrial systems include devices to help reduce the emission of undesirable substances. Such devices typically include an exhaust sensor that detects a level of undesirable substances in the exhaust stream. Exhaust sensors may be adapted to measure levels of oxygen, hydrocarbons and nitrous oxides in the exhaust stream. Sensors may also be used to sense, for example, when an exhaust gas content switches from rich to lean, or lean to rich. The output of the exhaust sensor may be used by a combustion control unit to improve the quality of the exhaust stream by controlling various combustion unit parameters.

Constituents of exhaust gas such as particulates, and water droplets may foul the exhaust gas sensing device, resulting in degraded performance of the emission control device. For example, a fouled sensor may have reduced ability to accurately detect the constituent components of an exhaust gas stream. Shielding the sensor from direct contact with large particulate matter in the exhaust stream may reduce the occurrence of sensor fouling.

While preventing fouling of the exhaust sensor is important, a countervailing design consideration is to ensure sufficient airflow in the vicinity of the exhaust gas sensor. Sufficient flow is required to allow the sensor to provide an accurate reading in a given response time to facilitate effective control of the combustion unit.

An improved system and method for balancing the competing design goals of providing sufficient flow past an exhaust gas sensor while protecting the sensor from being fouled by large particles in the exhaust stream is desirable.

SUMMARY

In accordance with one aspect of the present technique, an exhaust gas sensor system is provided. The exhaust gas sensor system includes an inner chamber disposed around a sensor element. The system further includes an outer chamber substantially disposed around the inner chamber to redirect a flow of an exhaust gas stream having an original direction by allowing the exhaust gas stream to strike a surface of the inner chamber to change the original direction of the flow to a substantially perpendicular direction relative to the original direction, then to substantially reverse the substantially perpendicular direction of the flow to create a substantially reversed flow within the inner chamber.

In accordance with another aspect of the present technique, an exhaust gas sensor system is provided. The exhaust sensor system includes a sintered metal filter that prevents exhaust gas particles from fouling a sensor element. The system further includes an electric source coupled to the sintered metal filter to heat the sintered metal filter to a temperature sufficient to remove the exhaust gas particles from the sintered metal filter.

In accordance with another aspect of the present technique, a method of operating an exhaust gas sensor system is provided. The method includes directing a flow of an exhaust gas stream having an original direction through an opening formed at one end of an outer chamber. The method further includes redirecting the flow of the exhaust gas stream having the original direction by allowing the exhaust gas stream to strike a surface of an inner chamber substantially disposed within the outer chamber to change the original direction of the flow to a substantially perpendicular direction relative to the original direction, then to substantially reverse the substantially perpendicular direction of the flow to create a substantially reversed flow within the inner chamber.

In accordance with another aspect of the present technique, a method of operating an exhaust gas sensor system is provided. The method includes directing a flow of an exhaust gas stream to a sensor element via a sintered metal filter so that exhaust gas particles are trapped within the sintered metal filter. The method further includes heating the sintered metal filter via an electric source to remove the accumulated exhaust gas particles from the sintered metal filter.

These and other features, aspects, and advantages of the present invention will become better understood when the following detailed description is read with reference to the accompanying drawings in which like characters represent like parts throughout the drawings.

DETAILED DESCRIPTION OF PREFERRED EMBODIMENTS

Figure 1:
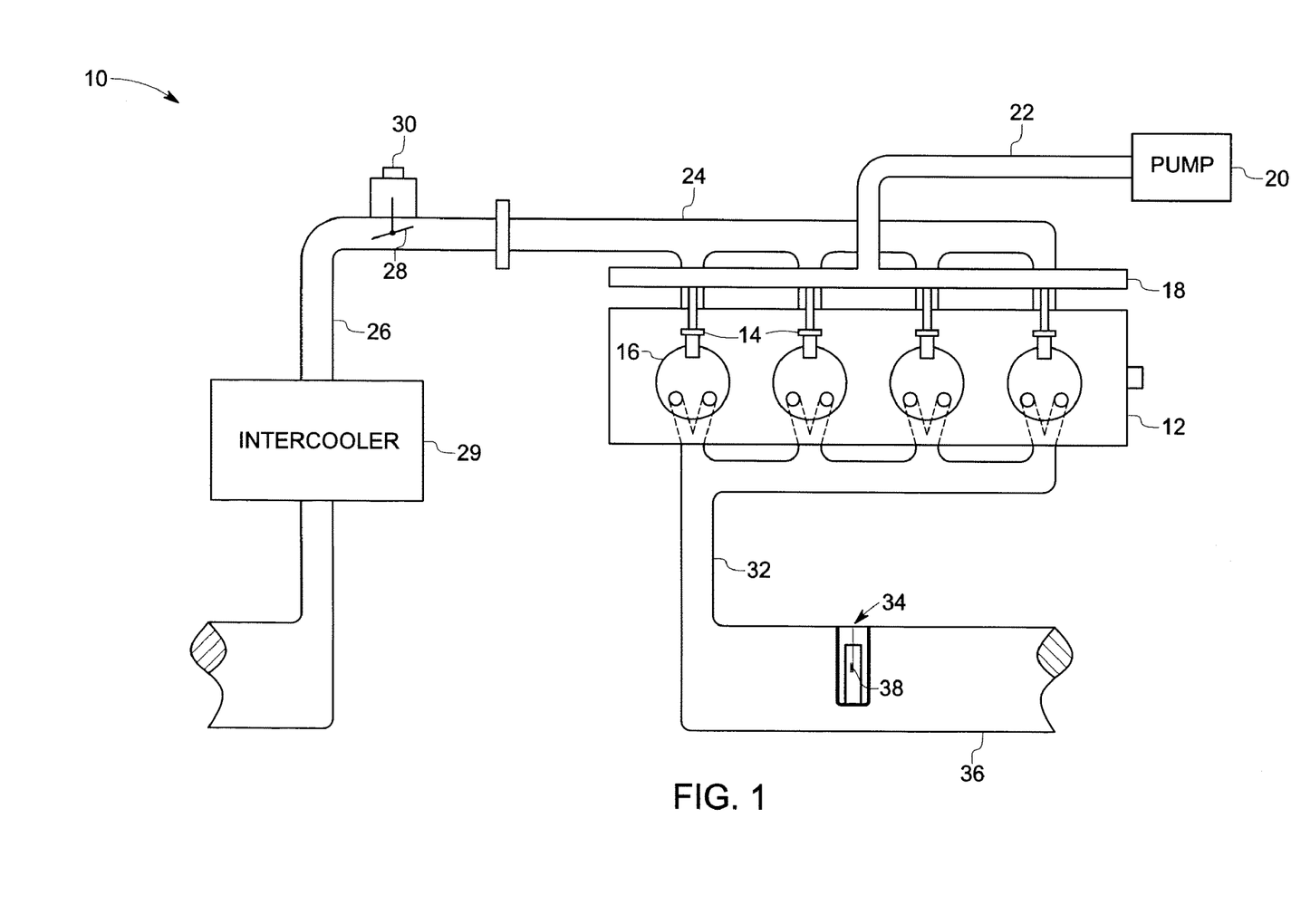
FIG. 1 is a diagrammatical representation of an internal combustion engine, having an exhaust gas sensor system in accordance with an exemplary embodiment of the present technique.

Referring to FIG. 1, a locomotive 10 having a combustion unit 12 such as an internal combustion engine is illustrated in accordance an exemplary embodiment of the present technique. The engine 12 includes a plurality of fuel injection valves 14, one for each cylinder 16. The fuel injection valves 14 are provided to inject fuel into a combustion chamber of each cylinder 16. The fuel injection valves 14 are coupled to an accumulator 18 configured to pressurize the fuel to a preselected pressure. The accumulator 18 is coupled to a fuel pump 20 via a fuel supply pipe 22.

An intake manifold 24 is coupled to the combustion chambers of the respective cylinders 16. The intake manifold 24 is coupled to an intake pipe 26. A throttle valve 28 is provided in the intake pipe 26 and located upstream of the intake manifold 24. The throttle valve 28 is configured to adjust flow rate of intake air through the intake pipe 26. An intercooler 29 is provided in the intake pipe 26 to cool the intake air through the intake pipe 26. A throttle actuator 30 such as a step motor may be coupled to the throttle valve 28 and configured to actuate the throttle valve 28.

An exhaust manifold 32 is coupled to the combustion chambers of respective cylinders 16. A fuel addition valve (not shown) may be provided in the exhaust manifold 32 for injecting fuel into the exhaust gas flowing through the exhaust manifold 32. An exhaust gas sensor system 34 is provided within an exhaust pipe 36 coupled to the exhaust manifold 32. The exhaust gas sensor system 34 may include an exhaust sensor element 38 adapted to measure levels of oxygen, hydrocarbons and nitrous oxides, or the like in an exhaust gas stream. Constituents of the exhaust gas stream such as soot particles, water droplets or the like may foul the exhaust sensor element 38 that may inhibit the ability of the sensor element 38 to detect the presence of gases effectively. The exhaust gas sensor system 34 includes features in accordance with the present technique, to protect the exhaust sensor element 38 against direct exposure to exhaust gases while helping to provide sufficient gas flow to the sensor element 38 to meet response time requirements necessary to effectively operate an engine control system.

In alternate embodiments, the exhaust gas sensor system 34 may be provided within an exhaust unit of an industrial system such as boilers, gas turbines, or the like. The exhaust gas sensor system 34 includes features in accordance with the present technique, to protect the exhaust sensor element 38 against exposure to exhaust gas particles such as soot particles, ash, or the like while helping to provide sufficient gas flow to the sensor element 38 to meet response time requirements necessary to effectively operate a combustion control unit.

Figure 2:
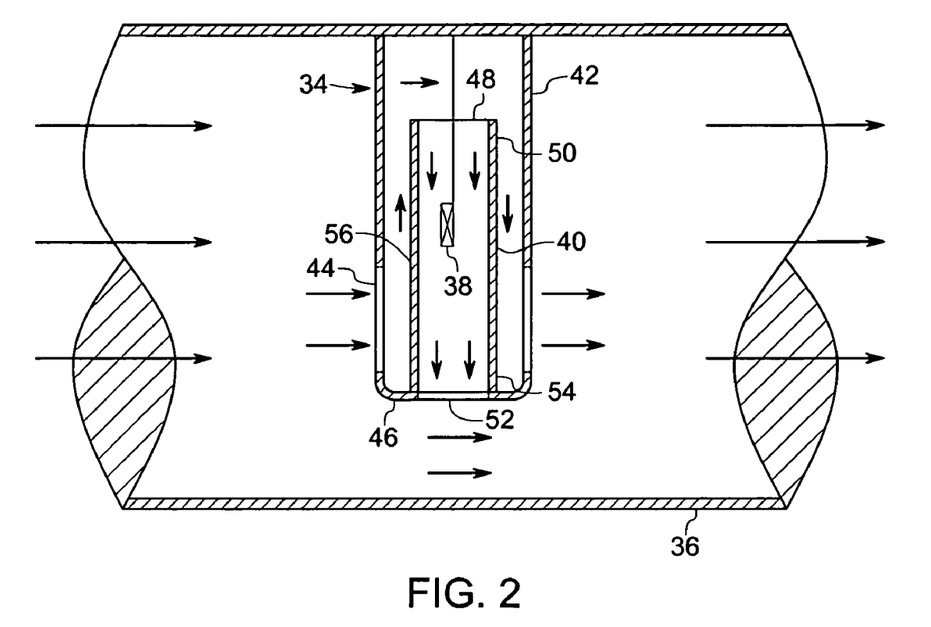
FIG. 2 is a diagrammatical representation of an exhaust gas sensor system having a cylindrical inner chamber inside an outer chamber in accordance with an exemplary embodiment of the present technique.

Referring to FIG. 2, the exhaust gas sensor system 34 provided inside the exhaust pipe 36 is illustrated in accordance with an exemplary embodiment of the present technique. In the illustrated embodiment, the system 34 includes a cylindrical inner chamber 40 disposed around the exhaust sensor element 38. A cylindrical outer chamber 42 is disposed around the inner chamber 40. An opening or a plurality of openings 44 are formed at one end 46 of the outer chamber 42 to allow passage of exhaust gas. In one example, the openings 44 are formed inclined at thirty degrees or sixty degrees in the outer chamber 42 to allow the passage of exhaust gas. An inlet opening 48 is formed at one end 50 of the inner chamber 40 and an outlet opening 52 is formed at another end 54 of the inner chamber 40 located proximate to the end 46 of the outer chamber 42. In the embodiment illustrated in FIG. 2, both the inner and outer chambers 40, 42 are substantially perpendicular to the direction of exhaust gas flow.

The outer chamber 42 is provided around the inner chamber 40 in such a way so as to redirect the flow of the exhaust gas stream. In the illustrated embodiment, the exhaust gas stream having an original direction (i.e. substantially perpendicular to the inner and outer chambers 40, 42) passes through the plurality of openings 44 in the outer chamber 42 and strikes a peripheral surface 56 of the inner chamber 40. The flow of the exhaust gas stream is redirected from the original direction to a substantially perpendicular direction relative to the original direction. The substantially perpendicular direction of the flow is then reversed to create a reversed flow within the inner chamber 40 by virtue of the fact that the exhaust gas stream enters through the inlet opening 48 and exits through the outlet opening 52 of the inner chamber 40. As a result, larger exhaust gas particles in the exhaust stream are prevented from entering the inner chamber 40 due to change in direction of the exhaust gas stream. Smaller particles in the exhaust gas stream reaching the sensor element 38 may be burned due to higher temperature prevailing around the sensor element 38. The exhaust gas particles may also be collected on the peripheral surface 56 of the inner chamber 40 due to thermophoresis effect. Thermophoresis occurs because of the movement of particles from a hotter region to a colder region. The exhaust sensor element 38 is protected from damage without compromising on the response time of the sensor element 38.

Figure 3:
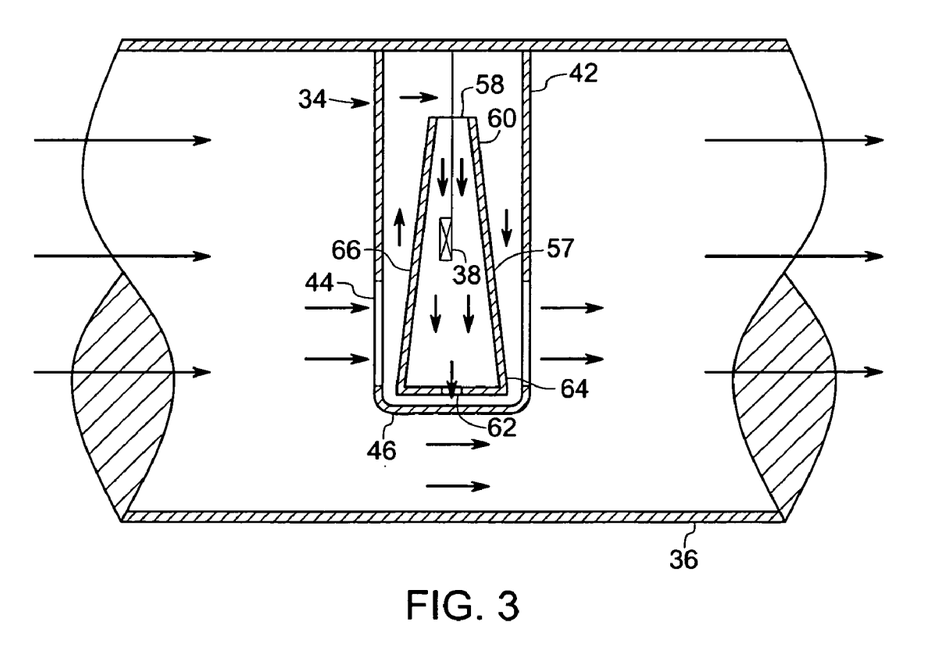
FIG. 3 is a diagrammatical representation of an exhaust gas sensor system having a frusto-conical shaped inner chamber inside an outer chamber in accordance with an exemplary embodiment of the present technique.

Referring to FIG. 3, the exhaust gas sensor system 34 provided inside the exhaust pipe 36 is illustrated in accordance with an exemplary embodiment of the present technique. In the illustrated embodiment, the system 34 includes a frusto-conical shaped inner chamber 57 disposed around the exhaust sensor element 38. The cylindrical outer chamber 42 is disposed around the inner chamber 57. The plurality of openings 44 are formed at one end 46 of the outer chamber 42 to allow passage of exhaust gas. An inlet opening 58 is formed at one end 60 of the inner chamber 57 and an outlet opening 62 is formed at another end 64 of the inner chamber 57. In the illustrated embodiment, a diameter of the outlet opening 62 is substantially smaller than a diameter of the inlet opening 58 to allow smooth flow of sensed gas. Both the inner and outer chambers 57, 42 are substantially perpendicular to the direction of exhaust gas flow.

As described above, the outer chamber 42 is provided around the inner chamber 57 in such a way so as to redirect the flow of the exhaust gas stream. In the illustrated embodiment, the exhaust gas stream having an original direction (i.e., perpendicular to the inner and outer chambers 57, 42) passes through the plurality of openings 44 in the outer chamber 42 and strikes a peripheral surface 66 of the inner chamber 57. The flow of the exhaust gas stream is redirected from the original direction to a substantially perpendicular direction relative to the original direction. The substantially perpendicular direction of the flow is then reversed to create a reversed flow within the inner chamber 57, i.e., the exhaust gas stream enters through the inlet opening 58 and exits through the outlet opening 62 of the inner chamber 57. As a result, larger exhaust gas particles in the exhaust stream are prevented from entering the inner chamber 57 due to a change in direction of the exhaust gas stream. The provision of frusto-conical shaped inner chamber 57 facilitates larger flow of exhaust gas into the inner chamber 57. The stagnation of exhaust gas between the inner chamber 57 and the outer chamber 42 is also reduced.

In the embodiments illustrated above, the inner chamber 57 is substantially enclosed within the outer chamber 42. As a result, the sensor element 38 is adequately protected. Moreover, the exhaust gas sensor system 34 is less susceptible to vibrational failures. Exhaust gas particles in the exhaust stream are prevented from entering the inner chamber 57 due to a change in direction of the exhaust gas stream. In one example, soot particles of size greater than fifty microns may be removed in the outer chamber 42.

Figure 4:
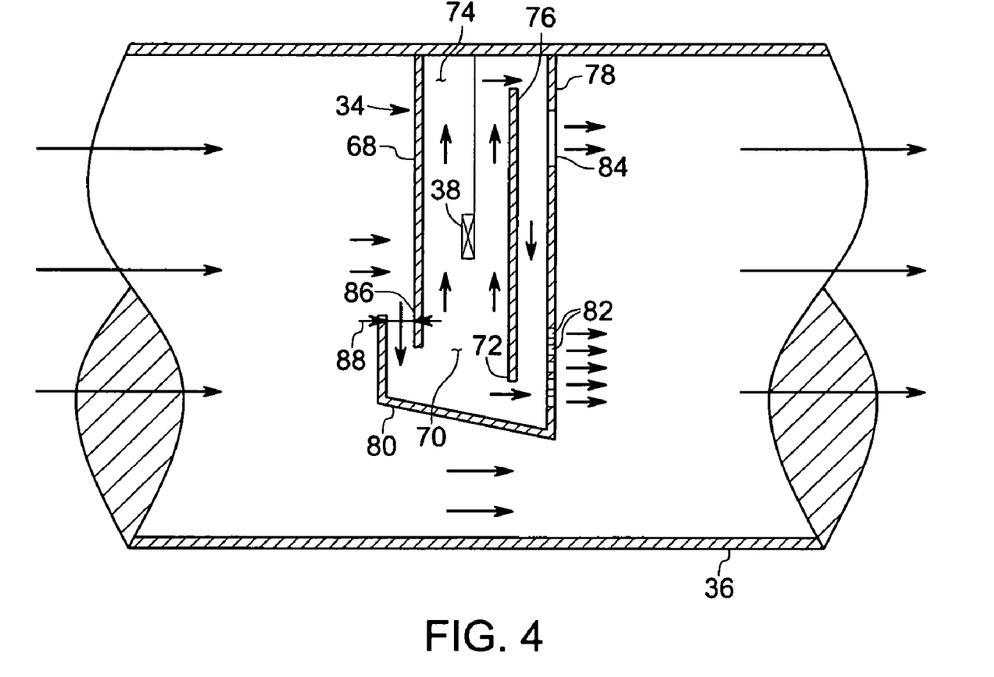
FIG. 4 is a diagrammatical representation of an exhaust gas sensor system having an inner chamber inside an outer chamber, wherein a periphery of the inner chamber is directly exposed to exhaust gas flow in accordance with an exemplary embodiment of the present technique.

Referring to FIG. 4, the exhaust gas sensor system 34 provided inside the exhaust pipe 36 is illustrated in accordance with an exemplary embodiment of the present technique. In the illustrated embodiment, the system 34 includes an inner chamber 68 disposed around the exhaust sensor element 38. An inlet opening 70 is formed at one end 72 of the inner chamber 68 and an outlet opening 74 is formed at another end 76 of the inner chamber 68. An outer chamber 78 is disposed around the inner chamber 68. One end 80 of the outer chamber 78 is inclined. A plurality of holes 82 are formed in the outer chamber 78 and located proximate to the end 80. The holes 82 are provided to drain the removed exhaust gas particles. The outer chamber 78 also has an outlet opening 84 for the exit of the exhaust gas. Both the inner and outer chambers 68, 78 are located perpendicular to the direction of exhaust gas flow in such a way that a periphery 86 of the inner chamber 68 is directly exposed to the exhaust gas stream.

The exhaust gas stream strikes the periphery 86 of the inner chamber 68 and enters through an annular gap 88 between the inner chamber 68 and the outer chamber 78. The exhaust gas stream is redirected from the inclined end 80 of the outer chamber 78 into the inner chamber 68. The exhaust gas passes through the inner chamber 68 and then exits through the outlet opening 84 formed in the outer chamber 78. As a result, larger exhaust gas particles in the exhaust stream are prevented from entering the inner chamber 68 due to change in direction of the exhaust gas stream. The exhaust gas particles are collected at the inclined end 80 of the outer chamber 80 and drained through the holes 82 formed in the outer chamber 78.

Figure 5:
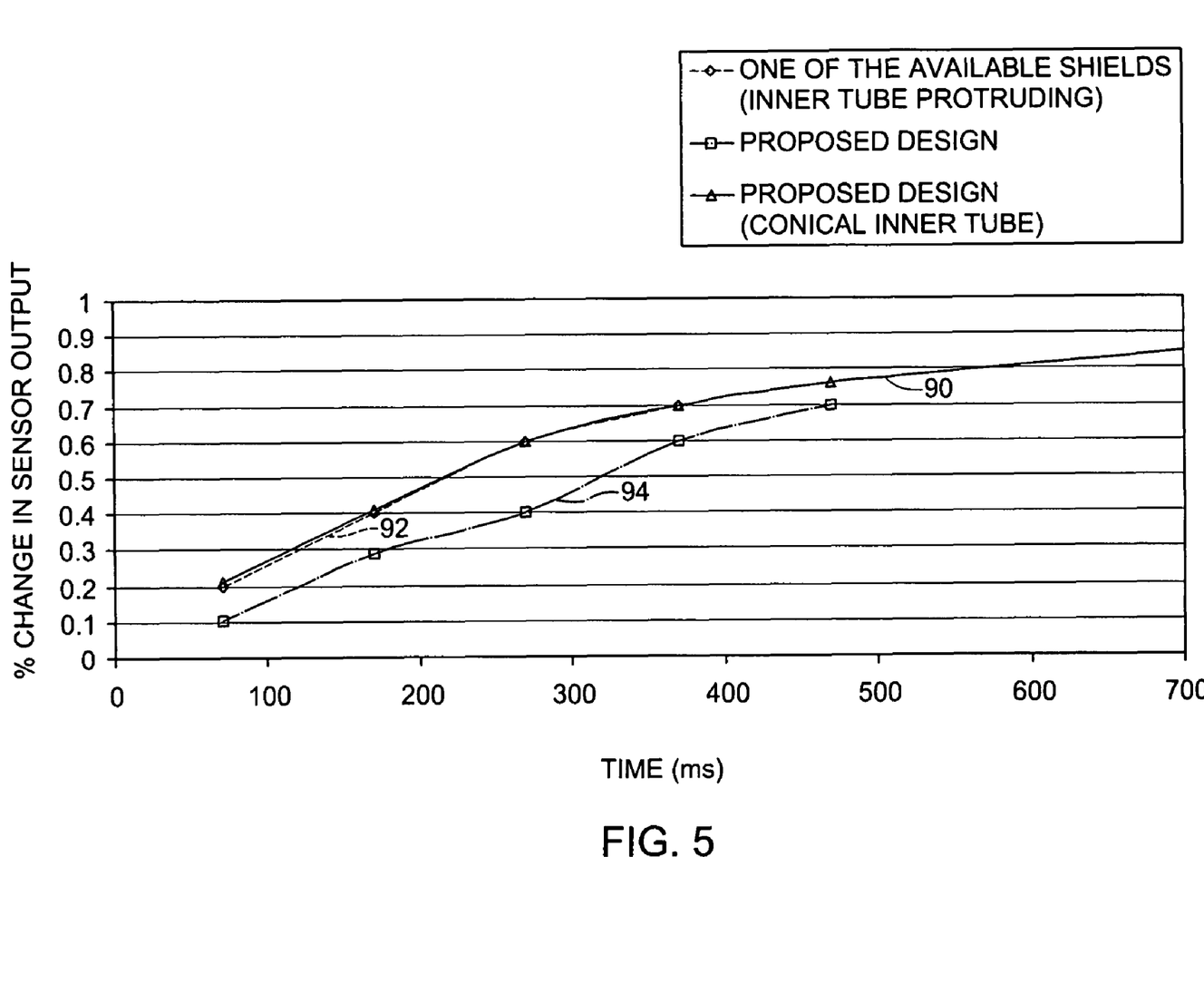
FIG. 5 is a graph illustrating variation of change in sensor output within an exhaust gas sensor system relative to time in accordance with an exemplary embodiment of the present technique.

Referring to FIG. 5, a graph illustrating variation of percentage change in sensor output within the exhaust gas sensor system 34 relative to time (in milli-seconds) in accordance with an exemplary embodiment of the present technique. A curve 90 illustrates variation of percentage change in sensor output of the exhaust gas sensor system 34 relative to time for given change in exhaust gas composition when the frusto-conical shaped inner chamber 57 is disposed within the outer chamber 42 in accordance with the exemplary embodiment illustrated in FIG. 3. Another curve 92 illustrates variation of percentage change in sensor output of the exhaust gas sensor system 34 relative to time for given change in exhaust gas composition when the inner chamber is protruding outwards from the outer chamber. Another curve 94 illustrates variation of percentage change in sensor output of the exhaust gas sensor system 34 relative to time for given change in exhaust gas composition when the cylindrical shaped inner chamber 40 is disposed within the outer chamber 42 in accordance with the exemplary embodiment as illustrated in FIG. 2. The response time of the exhaust gas sensor system 34 is dependent on the dimensions of the inner chamber and velocity of exhaust gas stream and is indicated by:

$$T \alpha \frac{h^2}{v \times D} \quad (1)$$

where T is the response time, h is height of inner chamber, v is the velocity of exhaust gas stream, and D is the diameter of the inner chamber.

It may be inferred from the graph that the sensor response time is improved when the diameter of the inner chamber is reduced. In accordance with the exemplary embodiment illustrated in the graph, the exhaust gas sensor system 34 in which frusto-conical shaped inner chamber 57 is provided within the outer chamber 42 gives a faster response. For example, for detecting about a seventy percent change in concentration of exhaust gas, the exhaust sensor element 38 takes approximately 400 milli-seconds.

Figure 6:
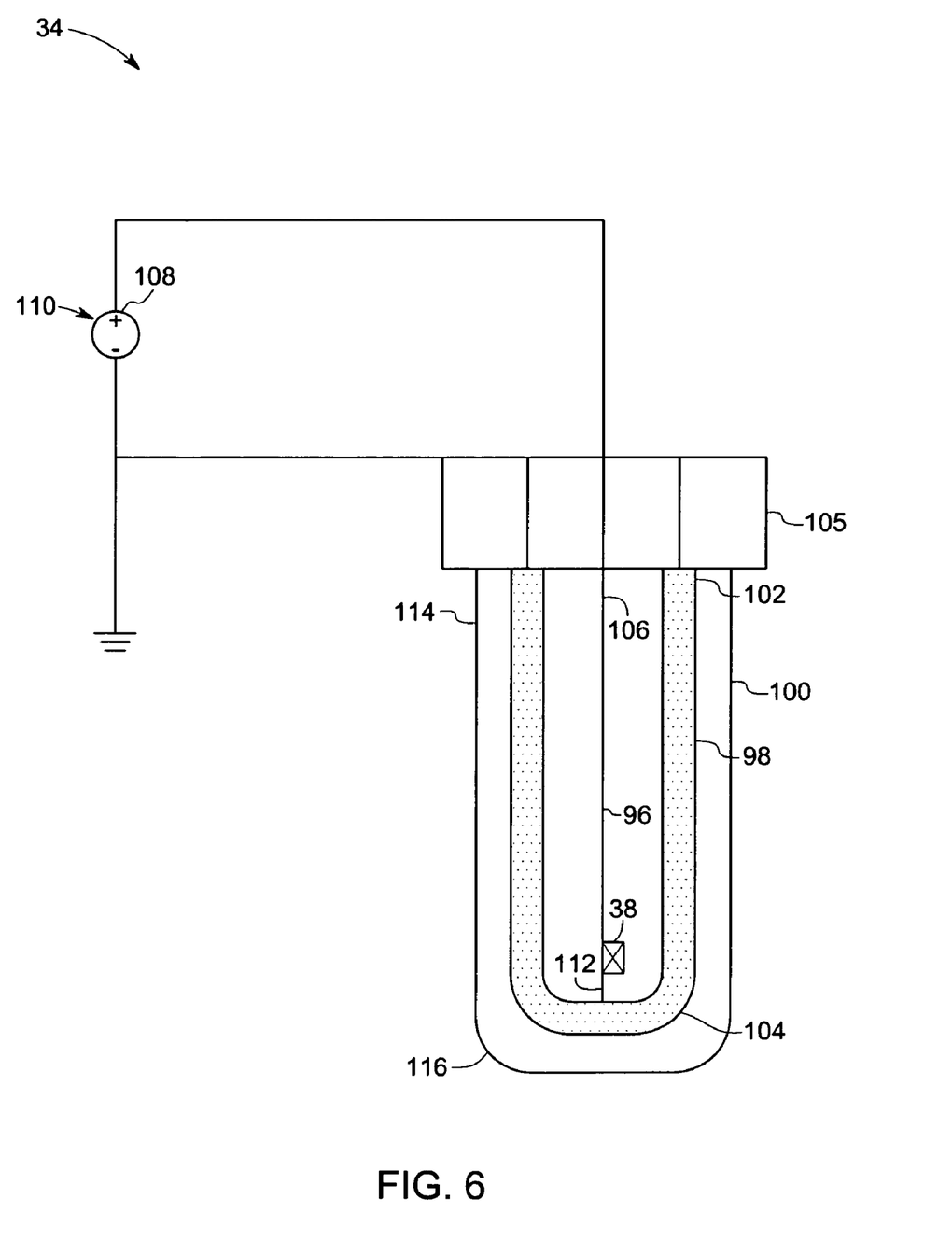
FIG. 6 is a diagrammatical representation of an exhaust gas sensor system having an electric source coupled to a sintered metal filter in accordance with an exemplary embodiment of the present technique.

Referring to FIG. 6, the exhaust gas sensor system 34 provided inside the exhaust pipe 36 is illustrated in accordance with an exemplary embodiment of the present technique. The exhaust gas sensor system 34 includes the exhaust sensor element 38 mounted on a substrate 96. The exhaust sensor element 38 is enclosed within a sintered metal filter 98 provided inside an outer protective shell 100. The filter 98 includes an open end 102 and a closed end 104. The open end 102 of the filter 98 is coupled to a bolt head 105. One end 106 of the substrate 96 is coupled to a positive terminal 108 of a DC source 110. Another end 112 of the substrate 96 is electrically coupled to the closed end 104 of the sintered metal filter 98. The bolt head 105 is grounded. The outer protective shell 100 includes an open end 114 and a closed end 116. The open end 114 of the outer protective shell 100 is also coupled to the bolt head 105.

The sintered metal filter 98 is configured to prevent exhaust gas particles from reaching the exhaust sensor element 38. The sintered metal filter 98 may comprise iron, chromium, nickel, steel, or a combination thereof. The sintered metal filter 98 may have high electrical resistivity and good heat conducting properties. Although in the illustrated embodiment the filter 98 is a closed end tube, the filter may have other suitable configurations in other embodiments. The outer protective shell 100 is provided to protect the filter 98 from external contaminants such as moisture, water, or the like. The outer protective shell 100 may include plurality of holes or slots for allowing passage of exhaust gas stream.

Figure 7:
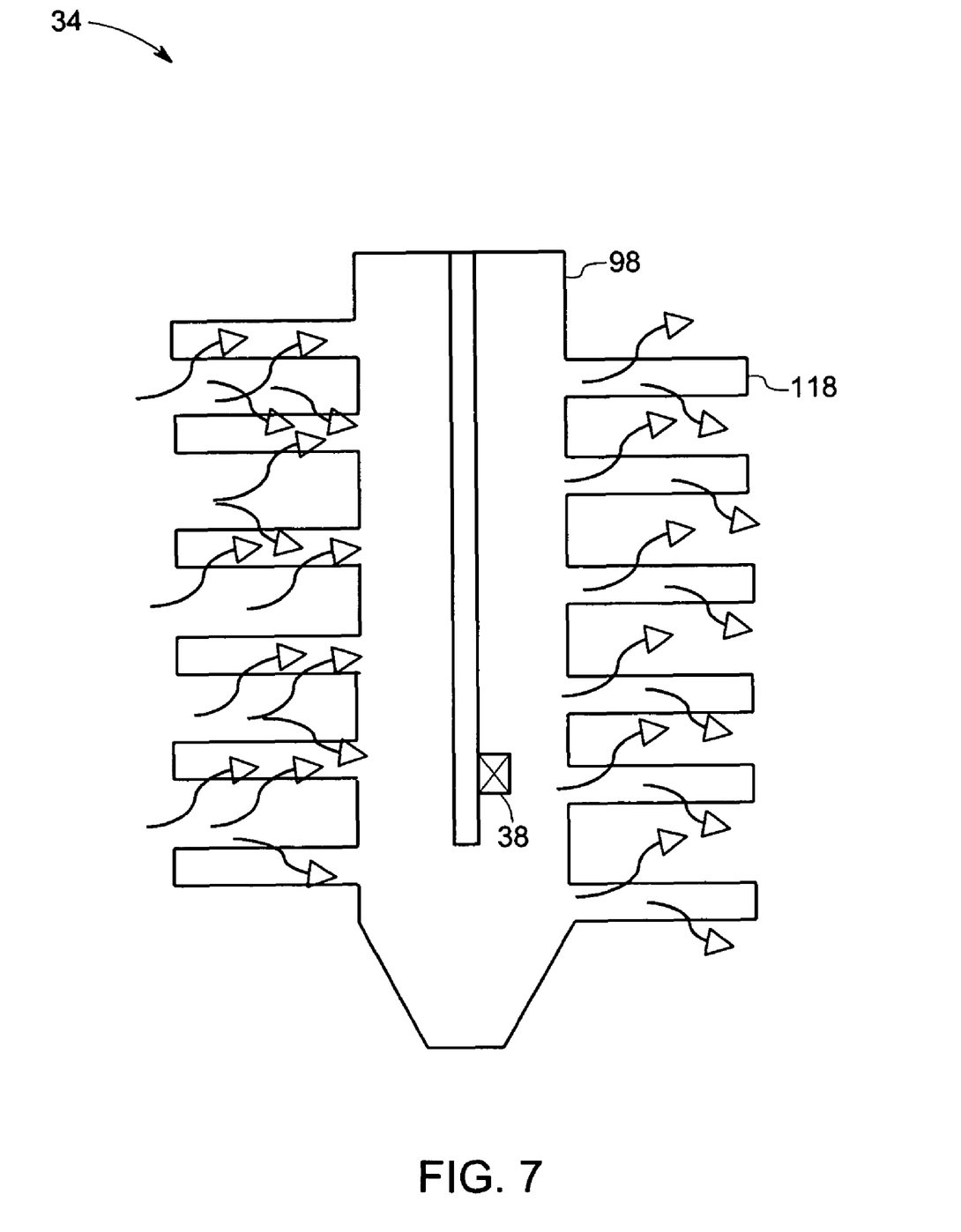
FIG. 7 is a diagrammatical representation of the exhaust gas sensor system having the sintered metal filter in accordance with the aspects of FIG. 6.

Referring to FIG. 7, the sintered metal filter 98 within the exhaust gas sensor system 34 is illustrated in accordance with an exemplary embodiment of the present technique. As discussed above, the sensor element 38 is mounted on the substrate 96 provided inside the sintered metal filter 98. In the illustrated embodiment, the filter 98 includes a sintered porous wall 118 configured to prevent the exhaust gas particles in the exhaust gas stream from reaching the sensor element 38 while ensuring sufficient gas flow to the sensor element 38 to meet response time requirements.

When the exhaust gas stream is passed through the sintered metal filter 98 to the sensor element 38, exhaust gas particles such as soot, ash particles, or the like within the exhaust gas stream is trapped within the filter 98. The filter 98 needs to be cleaned at predefined intervals or continuously to burn the soot particles trapped within the filter 98. If the filter 98 is not cleaned periodically, pressure drop across the filter 98 is increased, thereby reducing the amount of gas reaching the sensor element 38. As a result, response time of the sensor element 38 becomes slower. As discussed above, the current from the DC source 110 is passed through the filter 98 to directly heat the filter 98. Direct heating of the filter 98 enables the filter 98 to be maintained at higher temperatures to burn the soot particles trapped within the filter 98. In one example, the filter 98 may be maintained at a temperature in the range of 550 to 600 degrees Celsius to ensure the burning of soot particles. For industrial applications, a purge air source may be used to inject pressurized air to remove ash particles trapped within the filter 98.

Figure 8:
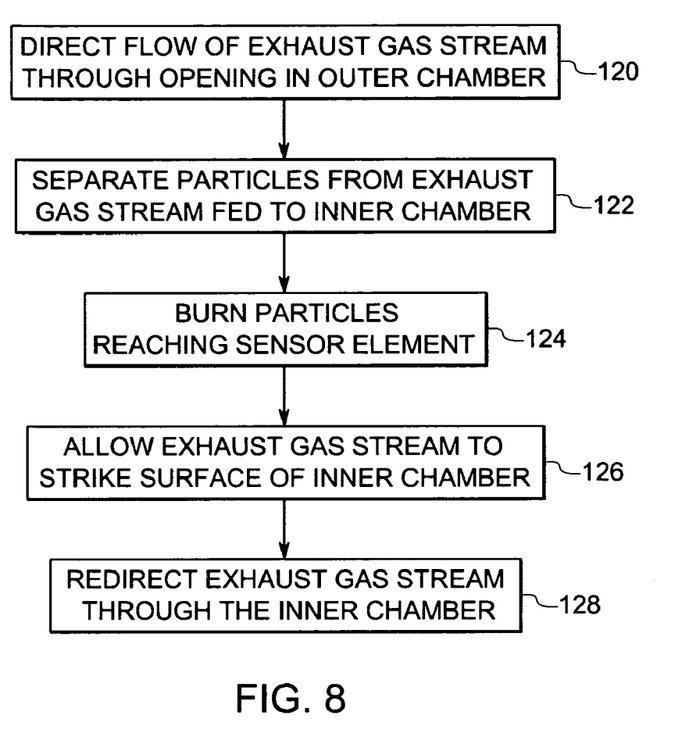
FIGS. 8 and 9 are flow charts illustrating exemplary processes of operating an exhaust gas sensor system in accordance with certain embodiments of the present technique.

Referring to FIG. 8, this figure is a flow chart illustrating a method of operating the exhaust gas sensor system 34 in accordance with an exemplary embodiment of the present technique. The method includes directing the flow of exhaust gas stream through the opening formed at one end in the outer chamber as represented by step 120. In one example, the exhaust gas stream is directed through plurality of openings formed at one end of the outer chamber. In one embodiment, the periphery of the inner chamber is directly exposed to the exhaust gas stream. The exhaust gas particles in the exhaust gas stream are separated from the exhaust gas stream fed to the inner chamber as represented by step 122. The particles reaching the exhaust sensor element is burned due to a higher temperature prevailing around the exhaust sensor element as represented by step 124. The separation of exhaust gas particles from the exhaust stream are explained in greater detail in subsequent steps.

The exhaust gas stream having an original direction is allowed to strike the peripheral surface of the inner chamber as represented by step 126. The exhaust gas stream is redirected to a change the original direction to a direction substantially perpendicular to the original direction. Thus, the gas stream flows axially via the gap between the inner and outer chambers. In one embodiment, the exhaust gas stream is redirected into the inner chamber by the inclined end of the outer chamber. The exhaust gas stream is then redirected through the inner chamber as represented by step 128. Thus, the exhaust gas stream enters through the inlet opening and exits through the outlet opening of the inner chamber. As a result, larger exhaust gas particles in the exhaust stream are prevented from entering the inner chamber due to change in direction of the exhaust gas stream.

Figure 9:
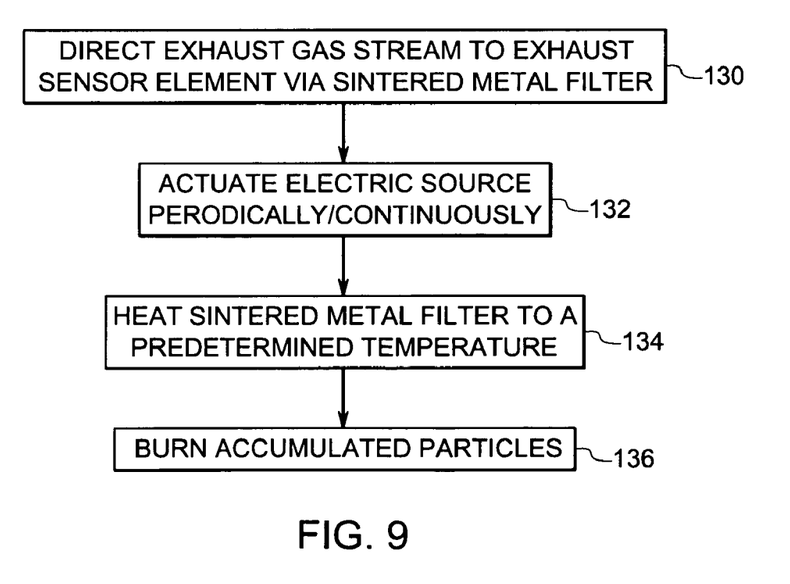

Referring to FIG. 9, this figure is a flow chart illustrating a method of operating the exhaust gas sensor system 34 in accordance with an exemplary embodiment of the present technique. The method includes directing an exhaust gas stream to the exhaust sensor element 38 via the sintered metal filter 98 as represented by step 130. The exhaust gas particles in the exhaust gas stream are trapped in the sintered metal filter 98. The DC source 110 is actuated periodically or continuously to directly heat the sintered metal filter 98 as represented by step 132. At step 134, the filter 98 may be heated to a predefined temperature in the range 550 to 600 degrees Celsius. The filter 98 is heated to burn the soot particles trapped in the sintered metal filter 98 as represented by step 136. Alternately, pressurized air may be injected to remove ash particles trapped in the metal filter 98. The particles in the exhaust gas stream are prevented from reaching the exhaust gas sensor element 38 while ensuring the passage of sufficient amount of exhaust gas to the exhaust sensor element 38.

While the invention has been described in detail in connection with only a limited number of embodiments, it should be readily understood that the invention is not limited to such disclosed embodiments. Rather, the invention can be modified to incorporate any number of variations, alterations, substitutions or equivalent arrangements not heretofore described, but which are commensurate with the spirit and scope of the invention. Additionally, while various embodiments of the invention have been described, it is to be understood that aspects of the invention may include only some of the described embodiments. Accordingly, the invention is not to be seen as limited by the foregoing description, but is only limited by the scope of the appended claims.

What is claimed as new and desired to be protected by Letters Patent of the United States is:

1. An exhaust gas sensor system, comprising:
  a sensor element;
  an inner conical chamber disposed around the sensor element; and
  an outer chamber having an inclined end for collecting exhaust gas particles, said outer chamber being substantially disposed around the inner chamber to redirect a flow of an exhaust gas stream having an original direction by allowing the exhaust gas stream to strike a surface of the inner chamber to change the original direction of the flow to a substantially perpendicular direction relative to the original direction, then to substantially reverse the substantially perpendicular direction of the flow to create a substantially reversed flow within the inner chamber.

2. The system of claim 1, wherein a periphery of the inner chamber is directly exposed to the exhaust gas stream.

3. The system of claim 1, wherein redirecting the flow of exhaust gas stream comprises separating particles from the exhaust gas stream fed into the inner chamber.

4. The system of claim 1, wherein redirecting the flow of exhaust gas stream comprises burning the particles reaching the sensor element.

5. A method of operating an exhaust gas sensor system, comprising:
  directing a flow of an exhaust gas stream having an original direction through an opening formed at one end of an outer chamber, said outer chamber having an inclined end for collecting exhaust gas particles; and
  redirecting the flow of the exhaust gas stream having the original direction by allowing the exhaust gas stream to strike a surface of an inner chamber substantially enclosed within the outer chamber to change the original direction of the flow to a substantially perpendicular direction relative to the original direction, then to substantially reverse the substantially perpendicular direction of the flow to create a substantially reversed flow within the inner chamber.

6. The method of claim 5, wherein redirecting the flow of the exhaust gas stream comprises entering the flow of the exhaust gas stream through one end of the inner chamber and exiting through the other end of the inner chamber.

7. The method of claim 5, wherein directing the flow of the exhaust gas stream comprises exposing a periphery of the inner chamber directly to the exhaust gas stream.

8. The method of claim 5, wherein redirecting the flow of the exhaust gas stream comprises redirecting the flow of exhaust gas stream to the inner chamber via an annular gap between the inner chamber and the outer chamber.

9. The method of claim 5, wherein redirecting the flow of exhaust gas stream comprises separating particles from the exhaust gas stream fed into the inner chamber.

10. The method of claim 5, wherein redirecting the flow of exhaust gas stream comprises burning the particles reaching the sensor element.

11. A system, comprising:
  a combustion unit;
  an exhaust unit coupled to the combustion unit and configured to eject exhaust gas generated from the combustion unit;
  an exhaust gas sensor system located in the exhaust unit, comprising:
  a sensor element;
  an inner chamber disposed around the sensor element; and
  an outer chamber having an inclined end for collecting exhaust gas particles, said outer chamber being disposed around the inner chamber to redirect a flow of an exhaust gas stream having an original direction by allowing the exhaust gas stream to strike a surface of the inner chamber to change the original direction of the flow to a substantially perpendicular direction relative to the original direction, then to substantially reverse the substantially perpendicular direction of the flow to create a substantially reversed flow within the inner chamber.

12. The system of claim 11, wherein the combustion unit comprises an engine.

13. The system of claim 12, further comprising a locomotive incorporating the engine.

* * * * *

UNITED STATES PATENT AND TRADEMARK OFFICE
CERTIFICATE OF CORRECTION

PATENT NO. : 7,739,898 B2
APPLICATION NO. : 11/166422
DATED : June 22, 2010
INVENTOR(S) : Shaddock et al.

Page 1 of 1

It is certified that error appears in the above-identified patent and that said Letters Patent is hereby corrected as shown below:

In Column 7, Line 63, in Claim 1, after "inner" delete "conical".

Signed and Sealed this

Twenty-third Day of November, 2010

David J. Kappos
*Director of the United States Patent and Trademark Office*